(12) United States Patent  
Radinsky et al.

(10) Patent No.: US 7,955,280 B2  
(45) Date of Patent: Jun. 7, 2011

(54) LEG ALIGNMENT FOR SURGICAL PARAMETER MEASUREMENT IN HIP REPLACEMENT SURGERY

(75) Inventors: Iliya Radinsky, Montréal (CA); Mélanie Chassé, Deux-Montagnes (CA); Louis-Philippe Amiot, Hampstead (CA); Daniel Odermatt, Montréal (CA)

(73) Assignee: Orthosoft Inc., Montréal, Québec (CA)

( * ) Notice: Subject to any disclaimer, the term of this patent is extended or adjusted under 35 U.S.C. 154(b) by 1133 days.

(21) Appl. No.: 11/421,572

(22) Filed: Jun. 1, 2006

(65) Prior Publication Data

US 2006/0293614 A1 Dec. 28, 2006

Related U.S. Application Data

(60) Provisional application No. 60/686,422, filed on Jun. 2, 2005, provisional application No. 60/693,830, filed on Jun. 27, 2005.

(51) Int. Cl.
*A61B 5/103* (2006.01)
*A61B 5/117* (2006.01)

(52) U.S. Cl. ......... 600/595; 600/587; 600/592; 600/594

(58) Field of Classification Search .................. 600/300, 600/587, 592, 594, 595; 623/11.11, 16.11, 623/18.11, 22.11, 22.12, 22.15, 22.4, 23.11, 623/23.15, 23.39, 66.1, 902, 908; 703/6, 703/11; 702/1, 19; 382/100, 110, 128, 130, 382/131, 132

See application file for complete search history.

(56) References Cited

U.S. PATENT DOCUMENTS

2004/0097952 A1 5/2004 Sarin et al.
2004/0230199 A1 11/2004 Jansen et al.

FOREIGN PATENT DOCUMENTS

| CA | 2226476 | 12/1996 |
|---|---|---|
| CA | 2182747 | 1/1997 |
| CA | 2443219 | 10/2002 |
| JP | 8-508652 | 9/1996 |
| JP | 9-173350 | 8/1997 |
| JP | 2004-529699 | 9/2004 |
| WO | WO-01/67979 | 9/2001 |
| WO | 03/073951 | 9/2003 |
| WO | 2004/030556 | 4/2004 |
| WO | WO-2004/030559 | 4/2004 |
| WO | WO-2005/023110 | 3/2005 |

OTHER PUBLICATIONS

Murphy, Stephen B., Ecker, Timo M, *Evaluation of a New Leg Length Measurement Algorithm in Hip Arthroplasty*,. Clinical Orthopaedics and Related Research, No. 463, p. 85-89, © 2007 Lippincott Williams & Wilkins.

*Primary Examiner* — Jeffrey G Hoekstra
(74) *Attorney, Agent, or Firm* — Ogilvy Renault LLP

(57) ABSTRACT

A CAS system and method comprises a first reference in fixed relation with the pelvis and a registration tool. A sensor apparatus tracks the first reference and tool. A controller unit receives tracking data for the first reference and tool. A calculator tracks the pelvic frame of reference, and the tool to produce a femoral frame of reference at two sequential operative steps. A reference orientation adjustor receives tracking data for the pelvic frame of reference to orient the femoral frame of reference in a reference orientation with respect to the pelvic frame of reference, and to produce a reference adjustment value as a function of the reference orientation. A surgical parameter calculator receives tracking data from the tool to calculate surgical parameters as a function of the reference adjustment value.

9 Claims, 4 Drawing Sheets

LEG ALIGNMENT FOR SURGICAL PARAMETER MEASUREMENT IN HIP REPLACEMENT SURGERY

CROSS-REFERENCE TO RELATED APPLICATIONS

This patent application claims priority on U.S. provisional Patent Applications No. 60/686,422, filed on Jun. 2, 2005, and No. 60/693,830, filed on Jun. 27, 2005, by the present applicants.

FIELD OF THE INVENTION

The present invention generally relates to computer-assisted hip replacement surgery and, more precisely, to surgical parameter measurement and adjustment in hip replacement surgery.

BACKGROUND OF THE INVENTION

Total hip replacement surgery involves the introduction of an artificial hip joint in a patient. The artificial hip joint typically consists of a pelvic implant and a femoral implant. The pelvic implant is a cup received in the acetabulum. The femoral implant consists of a spherical portion received at an end of a longitudinal implant portion, or a femoral implant secured to the resurfaced femoral head. In the first case, the longitudinal implant portion is introduced into the intramedullary canal of the resected femur, with the spherical portion being generally centered with respect to the previous position of the femoral head. Therefore, the femoral head (i.e., spherical portion of the femoral implant) and the cup (i.e., pelvic implant) coact to create the artificial hip joint.

Different output values are of concern in hip replacement surgery. In order to reproduce a natural and/or improved gait and range of motion to a patient, the position and orientation of the implants, the medio-lateral offset of the femur and the limb length discrepancy must be considered during surgery. The work of the surgeon during hip replacement surgery will have a direct effect on these output values, and a successful surgery will relieve pain, provide motion with stability and correct deformities.

There is no precise definition of the intraoperative limb length discrepancy (hereinafter "intraop-LLD") and intraoperative medio-lateral offset (hereinafter "intraop-MLO"). On the preoperative X-rays, surgeons usually measure preoperative limb length discrepancy (hereinafter "preop-LLD") along the vertical axis of the body as a relation between the interischial line of the pelvis and the lesser trochanter of the femur. Intraoperatively, in order to obtain reasonable measurements that are then possible to validate with X-ray measurements, the surgeons have to align the leg along the vertical axis of the body. This alignment is highly dependent on the surgeon skills and experience. Changes in adduction/abduction of the leg will significantly alter the measurement and introduce measurements errors.

The accuracy of the measurements rests heavily on the surgeon's ability to reposition the leg accurately before each measurement. Therefore, in order to obtain an accurate intraop-LLD and intraop-MLO measurement, the leg, after the implant reduction, must be realigned in the same orientation as before the dislocation. Again, changes in adduction/abduction, flexion/extension and rotation of the leg will significantly alter the measurement.

Failure to provide a robust and accurate method for leg length and offset measurement intraoperatively might lead to the postoperative leg length inequality. This in turn might lead to patient dissatisfaction and/or discomfort, functional impairment (low back pain, static nerve palsy, abductor weakness, dysfunctional gait), unstable hip joint, early mechanical loosening

SUMMARY OF THE INVENTION

It is an aim of the present invention to address the issues pertaining to the prior art.

It is a further aim of the present invention to provide a novel method for guiding an operator in measuring surgical parameters such as limb length discrepancy and medio-lateral offset intraoperatively in computer-assisted surgery.

Therefore, in accordance with the present invention, there is provided a method of measuring surgical parameters in computer-assisted surgery so as to guide an operator in inserting a hip joint implant in a femur, comprising the steps of: i) digitizing a frame of reference of the pelvis, the frame of reference of the pelvis being trackable in space for position and orientation; ii) digitizing a first frame of reference of the femur as a function of the frame of reference of the pelvis; iii) obtaining a reference orientation for the frame of reference of the femur with respect to the frame of reference of the pelvis; iv) digitizing a second frame of reference of the femur with respect to said reference orientation as a function of the frame of reference of the pelvis, after initiation of implant reduction; whereby surgical parameters associating the femur to the pelvis are measured as a difference between the first and second frames of reference of the femur.

Further in accordance with the present invention, there is provided a CAS system for measuring surgical parameters during hip replacement surgery to guide an operator in inserting a hip joint implant in a femur, comprising: at least a first trackable reference in fixed relation with the pelvis, the first trackable reference being trackable to form a pelvic frame of reference; a registration tool being trackable; a sensor apparatus for tracking at least the first trackable reference and the registration tool; and a controller unit connected to the sensor apparatus so as to receive tracking data for at least the first trackable reference and the registration tool, the controller unit having: a position and orientation calculator to calculate from the tracking data a position and orientation of at least the pelvic trackable reference to track the pelvic frame of reference, and of the registration tool to produce a femoral frame of reference at two sequential operative steps; a reference orientation adjustor connected to the position and orientation calculator so as to receive tracking data for the pelvic frame of reference, and the femoral frame of reference associated with at least the first trackable reference, to orient the femoral frame of reference in a reference orientation with respect to the pelvic frame of reference, and to produce a reference adjustment value as a function of the reference orientation; and a surgical parameter calculator receiving tracking data from the registration tool to calculate surgical parameters as a function of the reference adjustment value, the surgical parameters at the two sequential operative steps being related by the reference orientation.

BRIEF DESCRIPTION OF THE DRAWINGS

These and other features, aspects and advantages of the present invention will become better understood with regard to the following description and accompanying drawings wherein.

DESCRIPTION OF THE PREFERRED EMBODIMENT

Figure 1:
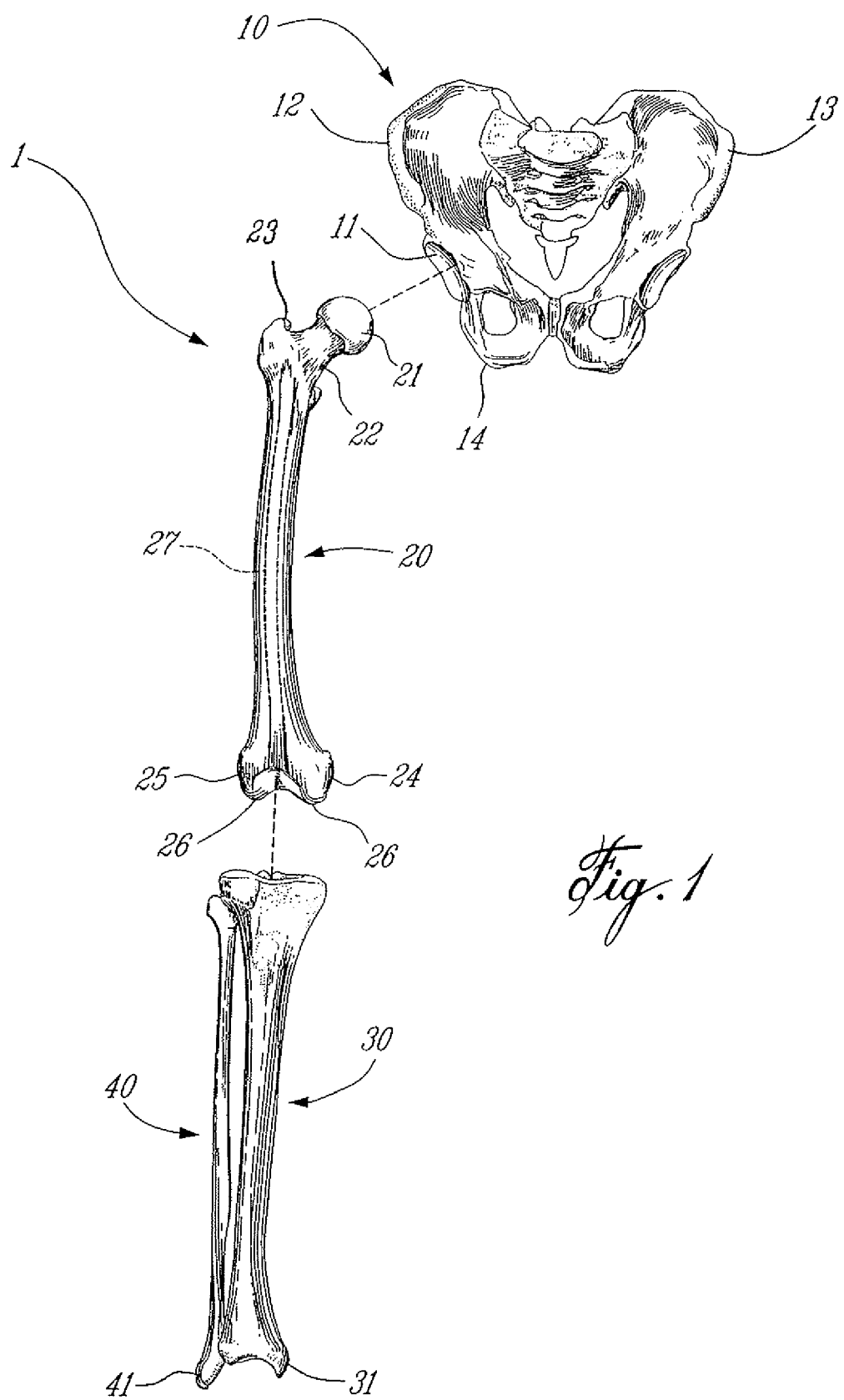
FIG. 1 is a front elevation view of leg bones involved in a hip replacement method in accordance with the present invention.

According to the drawings, and more particularly to FIG. 1, bones of the leg that are involved in the hip replacement surgery are generally shown at 1. FIG. 1 is provided as reference for the description of the steps of surgical parameter measurements associated with the hip replacement surgery method described herein. The bones are the pelvis 10, the femur 20, the tibia 30 and the fibula 40. Hereinafter, parts of these bones will each be referenced by numerals from the same numeric decade. For instance, parts of the pelvis (e.g., the acetabulum 11) will bear reference numerals between 11 and 19.

Figure 2:
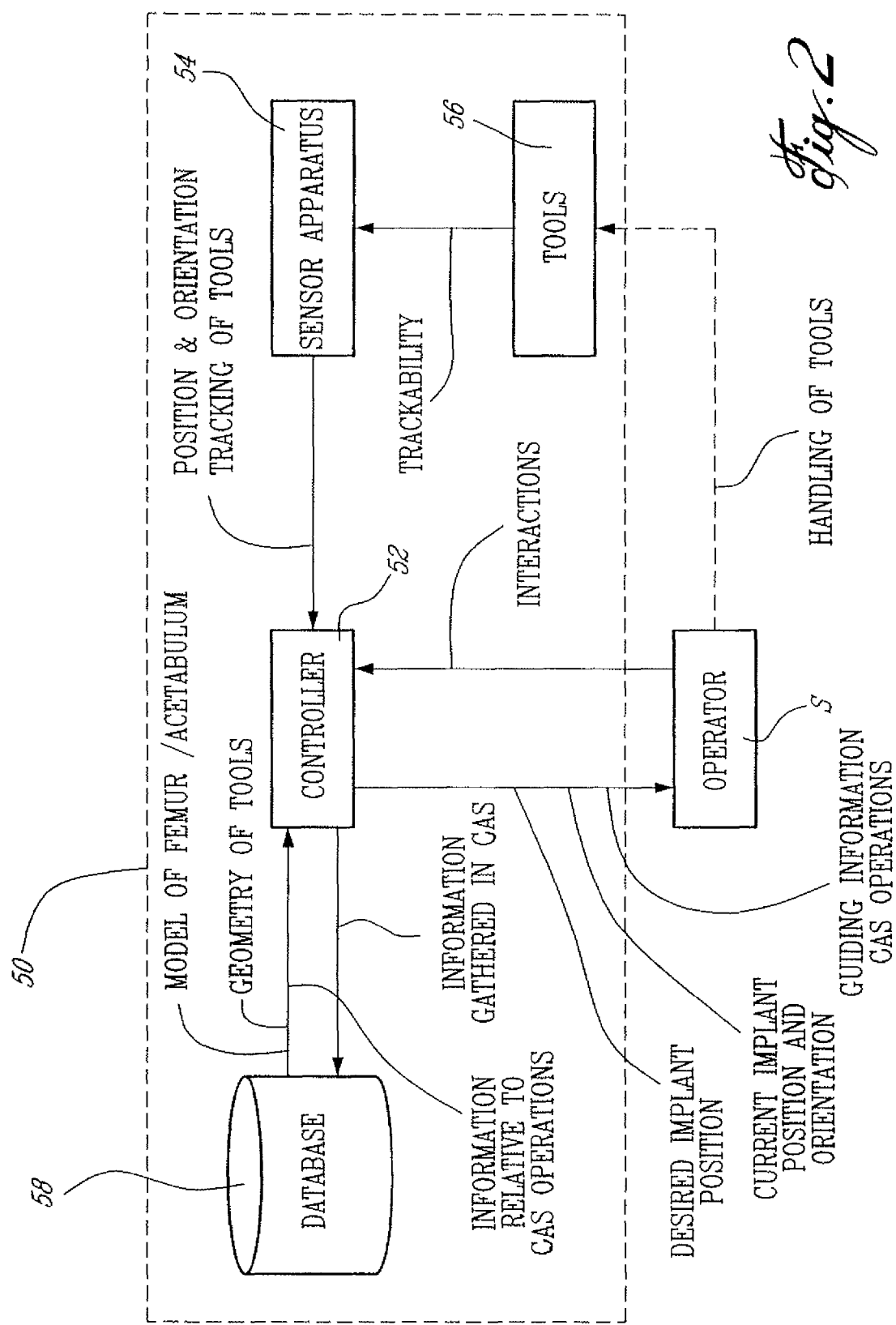
FIG. 2 is a block diagram of a computer-assisted surgery system in accordance with the present invention.

Referring to FIG. 2, a computer-assisted surgery system is generally shown at 50 (hereinafter CAS system 50) and generally consists of a CAS controller 52 connected to sensor apparatus 54. The sensor apparatus 54 tracks for position and orientation tools 56, to be described with the description of the parameter measurement method. The controller 52 is typically a PC unit that has user interfaces by which a surgeon will receive or send information that will guide him during the hip replacement surgery. For instance, monitors (e.g., touchscreen monitor), keyboard, mouse, and foot pedals are a few of the user interfaces that can be provided with the controller 52. A database of the controller 52 is illustrated separately as database 58, and is typically the hard disk drive of the controller 52.

Figure 3:
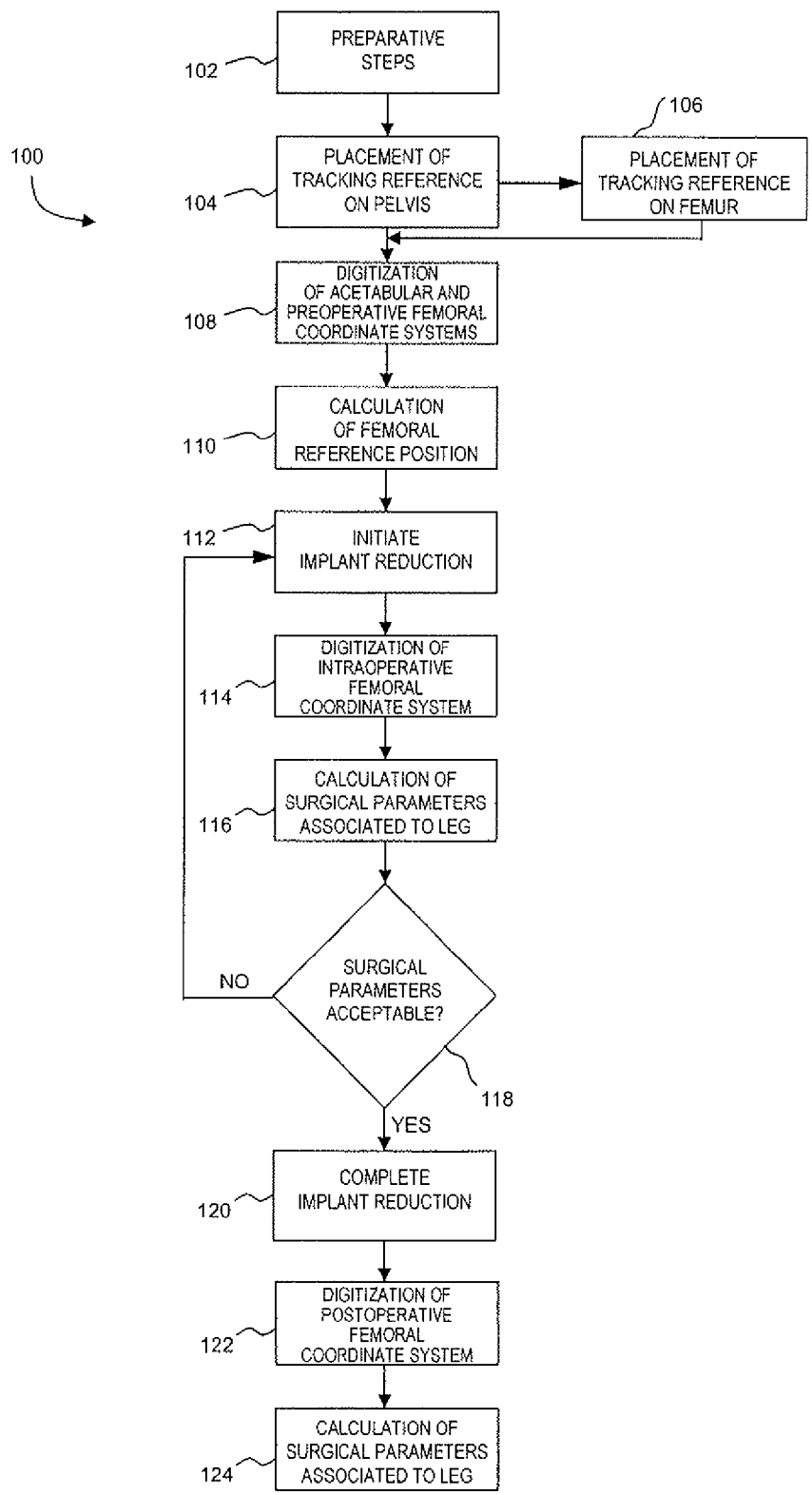
FIG. 3 is a flow chart of a method of hip replacement surgery in accordance with the present invention.

Referring to FIG. 3, a method for hip replacement surgery incorporating surgical parameter measurements in accordance with the present invention is generally shown at 100. It is pointed out that the method 100 is a hip replacement method incorporating additional surgical parameter measurement steps to provide the operator with supplemental information. Accordingly, the method 100 is associated with existing hip replacement methods, such as the method described in U.S. Publication No. 2004/0230199 by Jansen et al., published Nov. 18, 2004. Moreover, although the method 100 is described with a given sequence of steps, some digitizing steps may be suitably switched with surgical steps in accordance with the surgical method chosen by the operator. Although the method 100 is referred to in the singular, various choices of procedure will be given to the surgeon, as will be set forth in the forthcoming description, according to the preferences of the surgeon. A plurality of methods can be derived from the method 100 according to the decisions of the surgeon.

It is pointed out that the following definitions will be used in this document: pre-operative refers to the pre-dislocation period, intraoperative refers to the post-reduction period and postoperative refers to the post surgery period.

In Step 102, preparative steps for surgery are effected. Namely, general patient information can be entered into the CAS system 50 (FIG. 2) for opening a patient file. For instance, a general patient profile can be entered, that can consist of the name, birth date, identification number, sex and the like, as well as more specific data pertaining to the surgery, such as preoperative leg length discrepancy (with the identification of the longer leg), if applicable. For instance, the preoperative leg length discrepancy is measured using X-rays of the hip joint. More precisely, the leg length discrepancy is measured from the vertical comparison between the trochanters. These X-rays are typically taken during the diagnostic stages leading to surgery, so they are usually available for hip joint surgery. The calibration of the various surgical tools to be used is done. For instance, a calibration base and method, as set forth in International Publication No. WO 01/67979 A1 by Jutras et al., can be used for the calibration. Also, correspondence between the tracking of the tools 56 and the display on the CAS controller 52 can be verified in further calibration steps included in Step 102.

It is pointed out that the general patient information can be entered preoperatively. Moreover, the entering of the general patient information is straightforward such that the surgeon need not be involved. However, in order to minimize the preoperative procedures, all steps of method 100 can be performed at the beginning of the surgical session, during a short time span preceding the surgery.

Surgery is initiated between Step 102 and subsequent Step 104, by the surgeon exposing the hip joint. No computer assistance is required thereat.

In Step 104, a tracking reference (included in the tools 56) is secured to the pelvis 10. Therefore, the pelvis 10 can be tracked for position and orientation in space as a function of the tracking reference, by the CAS system 50 of FIG. 2.

In Step 106, another tracking reference is secured to the femur 20, for the tracking thereof for position and orientation. In order to reduce the invasiveness of the surgery, the use of a femoral tracking reference is optional, hence Step 106 is optional, as is illustrated in FIG. 3. The tracking references will remain anchored to their respective bones (if applicable) throughout the computer-assisted steps of surgery. The CAS system 50 must thus be adapted to track at least two tracking references simultaneously, and in real time. An interrelation between the two tracking references is preferably digitized at a given position of the leg. For instance, it is suggested to align the leg along the longitudinal axis of the body, and bend the knee at 90 degrees, to then digitize a relation between the trackable references.

Step 108 consists in the digitization of the acetabular and preoperative femoral coordinate systems, i.e., the acetabular frame of reference and the preoperative femoral frame of reference.

The acetabular coordinate system is digitized with a registration pointer from the tools 56. Various methods can be used to define an acetabular coordinate system. In one contemplated embodiment, three points are taken on the pelvis 10 to create the acetabular coordinate system. Referring to FIG. 1, there is one point on the iliac crest 12 of the operated side, one point on the contra lateral iliac crest 13, and one point on one of the two pubic tubercles 14 of the pelvis 10. To be generally aligned, the points digitized on the iliac crests 12 and 13 are taken at the outermost anterior point of the iliac crests 12 and 13. The points digitized on the iliac crests 12 and 13 are preferably taken directly on the soft tissue covering the bone pelvis on the iliac crests, as the soft tissue is relatively thin thereon. The point on the pubic tubercle 14 completes a first plane, the frontal plane (a.k.a. the coronal plane). A second plane, the transverse plane (a.k.a. the horizontal plane), is perpendicular to the frontal plane and includes the points on the iliac crests. A third plane, the sagittal plane, is perpendicular to the frontal and transverse planes.

Supplemental information regarding the frontal plane can be obtained for various postures of a patient, as described in International Publication No. WO 2004/030559 by Jansen et al., published on Apr. 15, 2004. For instance, trackable references can be used to gather information about sitting, standing and walking postures. This information can be used to adjust the orientation of the frontal plane, as these postures can provide information not available from the typical lying posture in which a patient is during surgery. This information can influence the anteversion positioning of the implants.

Also in Step 108, the preoperative femoral coordinate system is digitized. Various methods can be used to define the femoral coordinate system, and this will be dependent on whether a trackable reference is used for the femur (i.e., optional Step 106).

In one contemplated embodiment, the preoperative femoral coordinate system is defined by obtaining an anatomical axis, a mechanical axis and various planes for the femur 20. It is considered to provide five points of reference on the leg to the CAS controller 52, which is equipped with software that will create the femoral coordinate system.

Referring to FIG. 1, a first point is taken on the tip of the greater trochanter 23 of the femur 20, and will be defined as a starting point of an anatomical axis of the femur 20. Thereafter, points are taken on the medial and lateral epicondyles 24 and 25 of the femur 20, respectively. A midpoint between the medial epicondyle and lateral epicondyle points, in alignment therewith, is defined as an endpoint of the anatomical axis of the femur. Alternatively, a point on the patella can be digitized. The fourth and fifth points are taken on the medial malleolus 31 of the tibia 30 and on the lateral malleolus 41 of the fibula 40, with the leg being bent at the knee.

By having the leg bent at the knee, the tibia 30 stands on the posterior condyles 26 of the femur 20. Therefore, an assumption is made wherein an aligned midpoint of the medial and lateral malleoli points is said to define a plane (i.e., sagittal plane) with the anatomical axis, with an axis of the knee being normal to the sagittal plane. The frontal plane is perpendicular to the sagittal plane, with the anatomical axis lying therein. The transverse plane is perpendicular to the sagittal and frontal planes, and can be positioned at any height. It is noted that it is not required to measure two points to obtain a midpoint of the malleolus region. As this latter point will be in the sagittal plane, the only requirement is that a point is taken at a midpoint of the malleolus region, and may thus be placed approximately by the operator.

Also in Step 108, a registration of the mechanical axis of the femur, which will become a femoral reference axis, is performed. The registration of the mechanical axis will be dependent on whether only a tracking reference on the pelvis is used, as in Step 104, or whether the femur also supports a tracking reference, as optionally performed in Step 106.

For the purposes of method 100, the mechanical axis of the femur 20 passes through a midpoint of the medial and lateral epicondyles 24 and 25, as described in Step 108, and a center of rotation of the hip joint. The digitization of the center of rotation of the hip joint will be dependent on the number of tracking references, as exposed above (either one or two tracking references).

If only one tracking reference is used, namely with the pelvis, a temporary tracking reference is positioned in a stable manner to the femur 20, and rotational movements of the femur 20 with respect to the pelvis 10 are performed. Accordingly, these movements will enable the CAS system 50 to calculate a center of rotation of the hip joint 10, and an assumption is then made that the center of rotation of the femur 20 is coincident with the center of rotation of the acetabulum 11. The calculated center of rotation of the hip joint will then be associated with the tracking reference on the pelvis. This method for obtaining the center of rotation of the hip joint 10 can also be performed if a tracking reference is provided on the femur 20. It is also contemplated to track a reamer from the tools 56 (FIG. 2) so as to obtain, in view of the geometry of the reamer, a position for the center of rotation of the acetabulum 11.

Another method contemplated for obtaining the center of rotation of the hip joint 10 is to digitize points in the acetabulum 11 with respect to the tracking reference on the pelvis 10. This method also assumes that the centers of rotation of the femur and the pelvis are coincident. Some references, such as U.S. Publication No. 2004/0230199, have already exposed this method of obtaining the center of rotation of the hip joint 10.

If the femur is also provided with a tracking reference, the center of rotation of the femoral head can be determined by digitizing points on the surface of the femoral head, as exposed in U.S. Publication No. 2004/0230199. The mechanical axis passes through the center of rotation and the midpoint of the epicondyles 24 and 25.

Thereafter, in Step 110, this digitized mechanical axis must be registered with respect to the acetabular coordinate system in the femoral reference orientation in view of subsequent surgical parameter measurement. The reference orientation of the femur 20 may be defined as a plurality of positions. However, it has been identified that a reference orientation in which the mechanical axis is at a 3° orientation with respect to the vertical axis of the body in the pelvic frontal plane is well suited to represent a reference orientation for a standing posture of the patient. This reference orientation is registered virtually by the CAS system 50 with respect to the acetabular coordinate system, once the mechanical axis has been obtained.

Surgical parameter measurements will be based upon the femoral reference orientation. For instance, the point on the greater trochanter, as obtained when defining the anatomical axis of the femur 20 in Step 108, can be used as a landmark for the calculation of medio-lateral offset and limb length discrepancy from preoperative, intraoperative, as well as postoperative data.

In Step 112, the implant reduction is initiated. As mentioned previously, the Step 112 of implant reduction is dependent on the method of surgery chosen by the operator. Accordingly, few details are given herein, but reference is made to U.S. Publication No. 2004/0230199, in which a suitable method for performing the implant reduction is described.

Throughout implant reduction, the operator will need surgical parameter measurements to validate the work being performed. The alterations to the femur 20 and the acetabulum 11 will result in potential changes to the position of the center of rotation of the hip joint 10.

It is therefore necessary to redigitize the center of rotation to perform the surgical parameter measurements with respect to the landmark points (e.g., the anatomical axis point on the greater trochanter), and the leg must not be moved between the digitization of the landmarks if no trackable reference is provided on the femur.

Therefore, Step 114 consists in the digitization of an intraoperative femoral coordinate system. The object is to obtain an intraoperative center of rotation for the hip joint 10 so as to redefine the mechanical axis to refer this measurement to the femoral reference orientation acquired in Step 110. The digitization of intraoperative femoral coordinate system in Step 114 will be dependent on a plurality of factors, such as the presence of one or two tracking references, as well as the types of alterations performed in the implant reduction.

For instance, alterations may be performed to the acetabulum 11 in addition to the insertion of a femoral implant to replace the femoral head 21. In both these cases, the implants will potentially change the position of the center of rotation of the acetabulum 11 and the femoral head 21. Therefore, in order to redigitize the center of rotation of the acetabulum 11 if an acetabular implant is used, points may be digitized in the acetabular cup or liner implanted in the acetabulum 11. Alternatively, calibration tools can be inserted into the implanted hip joint so as to obtain the center of rotation of the acetabulum 11. One such calibration tool is described in International Publication No. WO 2005/023110, by the present assignee.

For the center of rotation of the femur 20, physical models of femoral implant are often provided to the operator for the modelization of the center of rotation of the femur 20. More specifically, the physical models represent different sizes of femoral implant, and are used to temporarily estimate the leg length and mediolateral offset.

With such physical models, the femur 20 is readily digitized, for instance, by digitizing surface points on the physical model inserted into the femur 20, or by reproducing a motion of the femur 20 with respect to the pelvis, with a tracking reference secured or positioned on the femur 20.

It is pointed out that the presence of a tracking reference on the femur 20 has an effect on the intraoperative step of digitizing a center of rotation for the femoral implant (i.e. ball head) 21. Calibration tools can be placed on the femoral implant (physical model if used) so as to obtain the center of rotation of the femoral implant. Alternatively, surface points may be digitized on the surface of the inserted implant. It is noted that in these cases the implant reduction is not required for subsequent calculation of the limb length discrepancy and medio-lateral offset, as the system simulates implant reduction by superimposing the acetabular implant COR and femoral implant COR.

It is therefore required to have a COR for the acetabulum, assumed to be the hip joint and possibly acquired with the calibration tool while the joint is dislocated, which COR will be used subsequently in the alignment of the femur in a selected orientation.

If no tracking reference is secured to the femur 20, the leg is reduced with its implant, and at least two points on the femur 20, excluding the femoral implant (i.e. ball head) center, must be digitized in Step 114 so as to complete the intraoperative femoral coordinate system. It is contemplated to mark points on the bone during the digitization of the preoperative femoral coordinate system in Step 108, at which points the registration pointer from the tools 56 (FIG. 2) will be used to digitize known points. It is pointed out that it is important to have the femur 20 immobilized when taking these points. Once these points are confirmed, they will be related to the same points as measured in Step 108, whereby the intraoperative femoral coordinate system will be completed.

With the intraoperative center of rotation of the hip joint 10 obtained by digitizing the center of rotation of the altered acetabulum with respect to the pelvic trackable reference, the intraoperative mechanical axis (i.e., from the intraoperative center of rotation to the midpoint of the epicondyles) is realigned digitally in the frontal plane with respect to the femoral reference orientation defined previously. As the alignment of the preoperative mechanical axis was calculated previously, the intraoperative and postoperative greater trochanter points can be aligned in the frontal plane with respect to the pelvic trackable reference.

Therefore, in order to perform the realignment procedure without any femoral trackable reference, the starting point of the anatomical axis obtained in Step 108 (i.e., on the greater trochanter) is redigitized with the reduced femur, whereby the limb length discrepancy can be calculated on the acetabular frontal plane as the vertical spacing between the preoperative and the intraoperative or postoperative landmark (e.g., greater trochanter). Similarly, the mediolateral offset can be calculated as the difference between the horizontal position of the landmarks in the frontal plane.

Accordingly, information will be provided to the operator, so as to guide the operator in the alterations to be performed on the femur 20 in view of the calculated surgical parameters.

In Decision 118, the limb length discrepancy and the medio-lateral offset calculated in Step 116 may prompt adjustment in the implant reduction 112. Ultimately, acceptable limb length discrepancy and medio-lateral offset will lead to Step 120 with the completion of the implant reduction.

Steps 122 and 124 relate to the calculation of postoperative surgical parameters. Following the description of Steps 114 and 116 respectively, Steps 122 and 124 are performed to obtain limb length discrepancy and medio-lateral offset from final measurements taken on the implants.

Various parameters considered during the method 100 are described below. The target leg length is a desired position for the femoral center of rotation, and is calculated as follows:

$$(\text{target leg length}) = \Delta_{LL\ x\text{-}ray} + \text{adjustment value}$$

where ($\Delta_{LL\ x\text{-}ray}$) is the initially acquired limb length discrepancy from the preoperative X-rays as described previously. The adjustment value is any value selected by the operator to correct the target leg length in view of the initially acquired limb length discrepancy.

Another guiding parameter to be provided to the surgeon is the current leg length discrepancy. The current leg length discrepancy, (current $\Delta_{LL}$), is calculated as follows:

$$(\text{current } \Delta_{LL}) = (GT_{intraop}) - (GT_{preop}) - (\text{target leg length}),$$

where ($GT_{intraop}$) is the intraoperative Y value of the greater trochanter point following the realignment procedure, ($GT_{preop}$) is the preoperative Y value of the greater trochanter point following the realignment procedure, and where (target leg length) has been calculated previously. The current leg length discrepancy can be displayed by the CAS system 50 as an overall leg length, or as a relative value between leg lengths, with the value 0 representing legs of equal length.

Another guiding parameter to be provided to the surgeon is the current medio-lateral offset. The current medio-lateral offset, (current $\Delta MLO$), is calculated as follows:

$$(\text{current } \Delta MLO) = (GT_{intraop}) - (GT_{preop})$$

where ($GT_{intraop}$) is the intraoperative X value of the greater trochanter point following the realignment procedure (Step 116), ($GT_{preop}$) is the preoperative X value of the greater trochanter point following the realignment procedure.

The anteversion of the femoral implant is represented by the angle between the intersection of the frontal plane and the transverse plane and a projection of the neck axis (anticipated for the femoral implant) onto the transverse plane (Step 108).

Another guiding parameter to be provided to the surgeon is the varus/valgus angle of the femoral implant, which is equivalent to the varus/valgus angle of the tracked rasp. The angle is measured between the projection of the intramedullary canal axis and the projection of the longitudinal rasp axis onto the femoral frontal plane (Step 108), and is displayed to the surgeon in degrees.

Another guiding parameter to be provided to the surgeon is the distance between the previous femoral center of rotation (i.e., digitized in Step 112) and the current femoral center of rotation. The current femoral center of rotation is calculated as a function of the femoral implant geometry (e.g., the ball head size) and the tracking of the rasp. The distance can be given in X, Y and Z values (e.g., in mm) according to the femoral coordinate system (Step 108).

Now that the method 100 has been described in detail, the CAS system 50 will be described in accordance with the preferred embodiment of the present invention.

Referring to FIG. 2, an operator (e.g., surgeon) is illustrated at S and is guided in performing surgery by the CAS system 50. More specifically, the operator S interacts with the controller 52 of the CAS system 50 using the user interfaces of the controller 52 (e.g., mouse, touchscreen display unit, keyboard, sound emitter). As shown in FIG. 2, the controller 52 will provide guiding information on the method 100 to the operator S throughout CAS. The guiding information is for instance retrieved by the controller 52 from the database 58, and will guide the operator S in handling the tools 56.

The tools 56 are each trackable in space for position and orientation by the sensing apparatus 54, such that a position and/or orientation of given components thereof are calculable. As a general basic requirement, the tools 56 include the reference tools, such as the trackable references securable to the bones (Steps 104 and 106), for the creation of frames of reference of the bones. Another one of the required tools 56 is a registration tool that will enable to gather surface information about the bones (e.g., Steps 110, 114, 116, etc.). As mentioned previously, the registration tool can be a registration pointer, a tracked photogrammetric sensor, or the like. Finally, a bone altering tool is included in the required tools 56, such as a reamer and a rasp, for which uses are associated with Step 112. Also, the tools 56 include the pelvic (impactor) and the femoral implant, that can be tracked for position and orientation, to guide the operator during the insertion. It is pointed out that information relating to the tools (e.g., geometry, position of tip) is either known by the controller 52 (or retrievable from the database 58) or determinable using various steps of calibration.

The sensing apparatus 54 is connected to the controller 52, and transfers position and orientation tracking to the controller 52. The position and orientation trackings are used by the controller 52 to calculate parameters pertaining to the CAS. More precisely, the position and orientation trackings of the reference tool and registration tool are used to create frames of reference of the pelvis and the femur, as described in Steps 110, 114 and 116. As shown in FIG. 2, the frame of reference information is provided to the operator S, for instance using the display unit of the controller 52.

For the pelvic implant, an initial center of rotation is calculated with respect to the frame of reference, as described in Step 108. The acetabular center of rotation will be used with the pelvic frame of reference as references for the alteration of the acetabulum in view of the insertion of the pelvic implant therein. The database 58 stores information that is retrieved by the controller 52 to make the calculation.

The current pelvic and femoral implant positions and orientations are calculated as a function of the position and orientation tracking of the bone altering tools, and of the geometry of the respective implants. Once more, the controller 52 uses the output of the sensor apparatus 54 and information stored in the database 58 for the calculations, that will be displayed for guiding the operator S.

The CAS system 50 can operate with active or passive tracking. In a preferred embodiment of the present invention, the sensor apparatus 54 is a NDI Polaris® optical tracking apparatus, with appropriate operating software in the controller 52. With the Polaris® optical tracking apparatus, passive detectable devices, such as retro-reflective spheres, are used in patterns to be tracked in space for position and orientation. Each one of the tools 56 that requires to be tracked has an own detectable pattern.

The CAS system 50 must guide the surgeon throughout the method 100, and relevant information is displayed to ensure the surgeon follows the proper Steps of operation. For instance, when leg length discrepancy values are given, the cranial-caudal convention can be displayed to explain the reading obtained. Animations can be initiated automatically to guide the surgeon, for example, in taking reference points on the various bones, such that the reference points are taken in a given order, or at the right locations.

Figure 4:
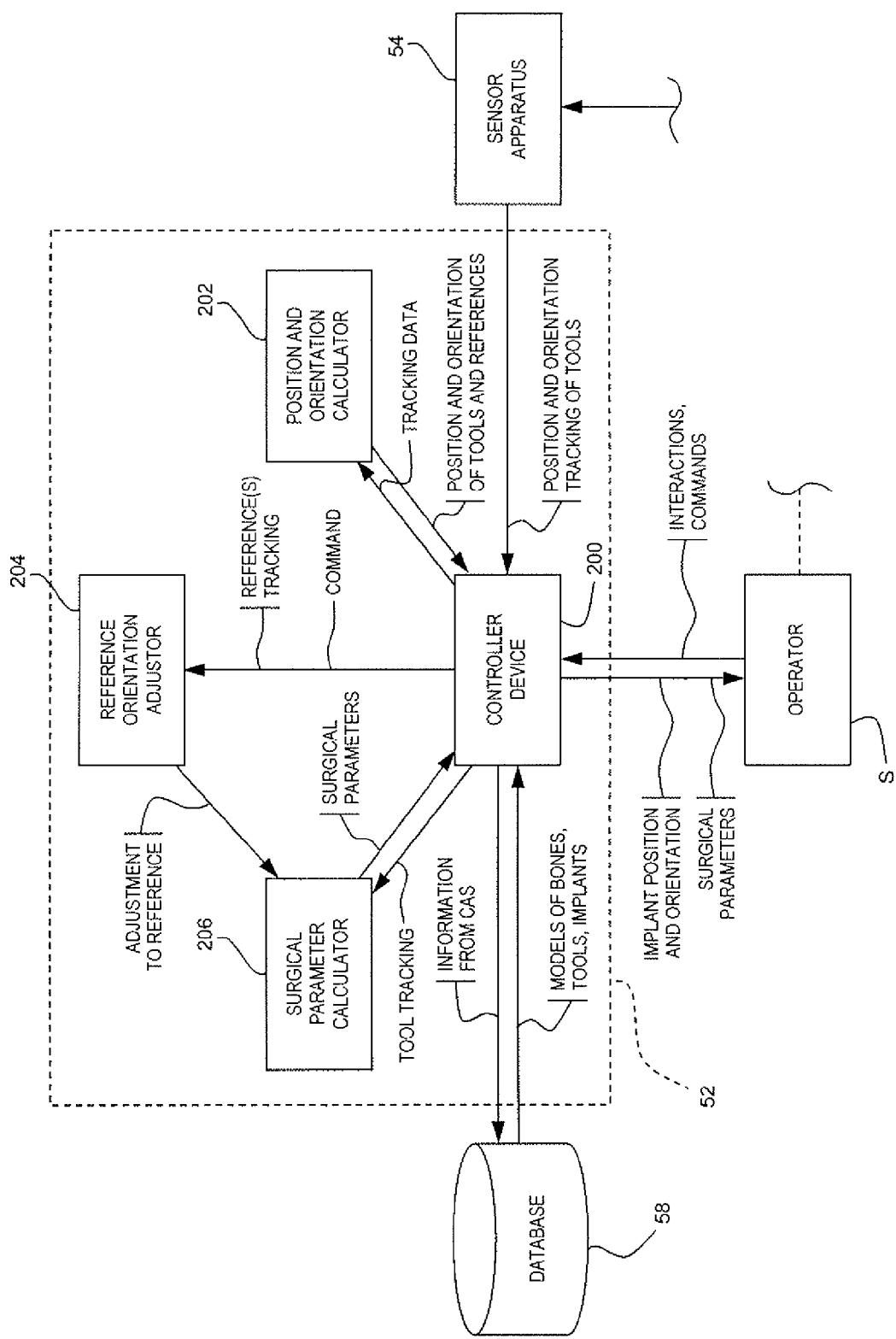
FIG. 4 is a block diagram of a controller device of the computer-assisted surgery system of FIG. 2.

Referring to FIG. 4, the CAS controller 52 is shown in greater detail. The CAS controller 52 typically is a processing unit having a controller device 200 which processes the information. The controller device 200 is connected to the sensor apparatus 54 so as to receive position and orientation tracking data of tools, such as the trackable references and the registration tool.

A position and orientation calculator 202 receives the tracking data, and calculates position and orientation of tools, as well as frames of reference. Therefore, the controller device 200 allows the operator S to perform the surgery in real-time CAS navigation.

In order to compare points taken pre-operatively with points taken intra-operatively and post-operatively according to the method 100, a reference orientation adjustor 204 is provided in association with the controller device 200. More specifically, updates to data associated with the femoral frame of reference are received by the reference orientation adjustor 204. When the information is complete, the reference orientation adjustor 204 calculates a reference adjustment value that consists in the realignment of the re-digitized frame of reference to the reference orientation. As mentioned previously, this consists in positioning the mechanical axis (with the intraoperative or post-operative center of rotation) at a predetermined angle to the vertical axis in the frontal plane of the pelvic frame of reference, with the centers of rotation of the femur and acetabulum in a known relation.

The reference adjustment value is then provided to a surgical parameter calculator 206, which will calculate surgical parameters taken into account the reference adjustment value. Therefore, no physical alignment is required considering that the CAS controller 52 performs all alignment virtually.

We claim:

1. A method of measuring surgical parameters in computer-assisted surgery so as to guide an operator in inserting a hip joint implant in a femur, comprising:
   i) digitizing a frame of reference of a pelvis, the frame of reference of the pelvis being trackable in space;
   ii) digitizing a pre-reduction frame of reference of the femur as a function of the frame of reference of the pelvis, the pre-reduction frame of reference comprising a femoral axis;
   iii) obtaining a reference orientation for the femoral axis of the pre-reduction frame of reference of the femur with respect to the frame of reference of the pelvis;
   iv) digitizing a reduction frame of reference of the femur by virtually orienting the femoral axis in said reference orientation as a function of the frame of reference of the pelvis, after initiation of implant reduction;
   v) providing the surgical parameters associating the femur to the pelvis and measured as a difference between the first and second frames of reference of the femur.

2. The method according to claim 1, wherein the femoral axis is a mechanical axis, and wherein obtaining a the reference orientation comprises the reference orientation having the mechanical axis of the pre-reduction frame of reference of the femur at a predetermined angle of a vertical axis of a patient within a frontal plane of the frame of reference of the pelvis.

3. The method according to claim 2, wherein obtaining the reference orientation comprises the reference orientation having the mechanical axis where the predetermined angle is 3°.

4. The method according to claim 2, wherein digitizing the frame of reference of the pelvis comprises digitizing two points on an iliac crest and a point on one of pubic tubercles to obtain the frontal plane of the frame of reference of the pelvis.

5. The method according to claim 2, wherein obtaining the reference orientation comprises having the mechanical axis of the pre-reduction frame of reference of the femur pass through a center of rotation of the femur, and the reference orientation has the center of rotation of the femur and of an acetabulum coincident.

6. The method according to claim 1, wherein the step iv) includes updating the frame of reference of the pelvis by digitizing a center of rotation of the acetabulum subsequently to the implant reduction.

7. The method according to claim 1, wherein the surgical parameters are at least one of a limb length discrepancy and a medio-lateral offset.

8. The method according to claim 1, wherein the steps i) and ii) are performed with respect to a single trackable reference secured to the pelvis.

9. The method according to claim 1, wherein the method is performed on a bone model or a cadaver.

* * * * *